United States Patent [19]

Hertzer

[11] Patent Number: 4,846,794
[45] Date of Patent: Jul. 11, 1989

[54] COILED TUBING FOR INTRAVENOUS AND INTRA-ARTERIAL APPLICATIONS

[75] Inventor: Norman R. Hertzer, Chagrin Falls, Ohio

[73] Assignee: The Cleveland Clinic Foundation, Cleveland, Ohio

[21] Appl. No.: 85,459

[22] Filed: Aug. 13, 1987

[51] Int. Cl.⁴ ............................................. A61M 5/00
[52] U.S. Cl. ..................................... 604/83; 604/257
[58] Field of Search ................ 604/93, 251, 257, 262, 604/83, 284; 138/118

[56] References Cited

U.S. PATENT DOCUMENTS 2,447,691  8/1948  Evans .
3,021,871  2/1962  Rodgers .
3,288,169  11/1966 Moss .
4,009,734  3/1977  Sullivan .
4,069,881  1/1978  Shiber .
4,160,466  7/1979  Jousson .
4,292,969  10/1981 Raible et al. .
4,547,191  10/1985 Ichikawa et al. ................... 604/251
4,699,613  10/1987 Donawiki ............................ 604/257

Primary Examiner—Stephen C. Pellegrino
Attorney, Agent, or Firm—Fay, Sharpe, Beall, Fagan, Minnich & McKee

[57] ABSTRACT

A tube for intravenous and intra-arterial applications includes a resilient conduit which is helically coiled along substantially its entire length. The conduit is preformed into a helical coil configuration so that when the conduit is in an unstressed condition, it assumes the helical coil configuration.

9 Claims, 1 Drawing Sheet

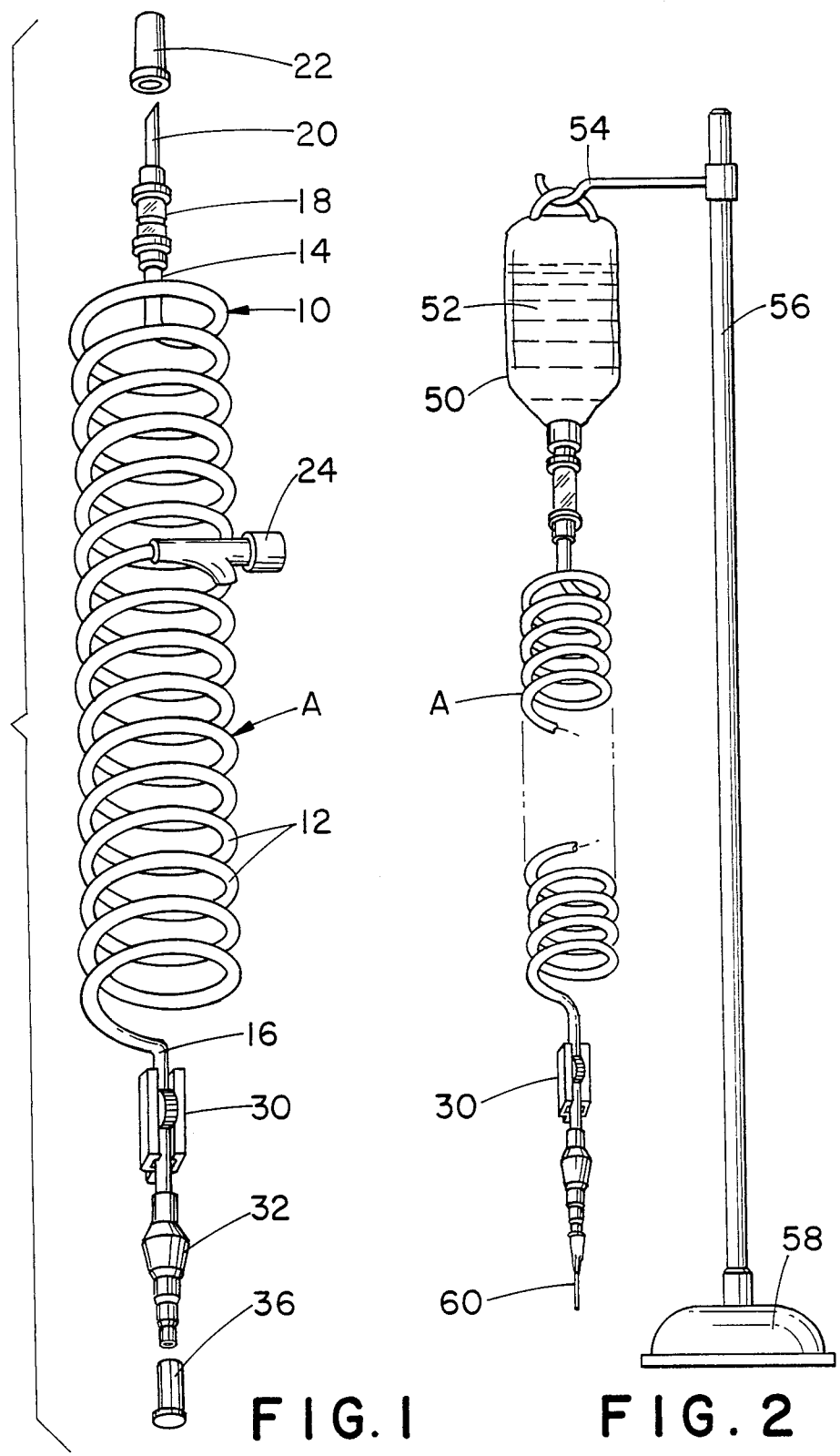

COILED TUBING FOR INTRAVENOUS AND INTRA-ARTERIAL APPLICATIONS

BACKGROUND OF THE INVENTION

This invention relates generally to fluid transmission conduits. More specifically, the present invention relates to a tube for intravenous and intra-arterial applications.

The invention can be designed for use in parenteral administration systems which are utilized to transfer intravenous solutions to medical patients. Such systems typically use a fluid supply container, a parenteral needle and tubing interconnecting the fluid supply with the needle. Transfer of the solution is achieved through gravity by suspension of the container above the patient. It should, however, be recognized that the present invention could also be adapted for use in various other intravenous infusion applications such as peripheral lines which are used to transfer blood or medicine to a patient. One such use is in administering anesthesia solutions to a patient during surgery. Also, the invention could be used for intra-arterial lines or Swan-Ganz lines which are used to measure blood pressure or cardiac function during surgery. Other intra-arterial lines are sometimes used with high-risk patients such as patients in intensive care after cardiac surgery or after transplants, such as a liver transplant.

In parenteral administration systems a plastic flask or a bottle is suspended from an elevated hook at a level above the patient and the liquid flows by gravity from the flask through a long flexible plastic tube on the free end of which is a discharge terminal, either in the nature of a needle or a catheter entered into a patient's vein, usually, but not necessarily, in the forearm. One difficulty with the tubing utilized in such conventional parenteral systems is that the tubing needs to be sufficiently long to afford the patient some room to move; but since the tubing is limp, it hangs straight down and becomes entangled in the bedrails, sheets and pillowcases of the patient who may be sitting or reclined in a bed. Additionally, the parenteral tubing can become entangled in nasogastric tubes or in other intravenous lines. The patient's range of movement is, moreover, absolutely restricted by the length of the tubing provided with the parenteral system. If the patient needs to go further, e.g. to the bathroom, the entire system must accompany him.

In an operating room environment the use of a number of different lines of tubing has been found necessary. These may include peripheral, parenteral, arterial, and CVP (central venous pressure) lines as well as catheter lines (e.g. Broviac or Hickman catheters). Additionally, sometimes a number of anesthesia solution lines need to be used. Conventional tubing utilized by an anesthesiologist, since it is limp, has a tendency to collect on the floor and loop around the ether screen or become hopelessly ensnarled in other tubing. This makes it difficult for the anesthesiologist to pull out the correct line of tubing for a particular purpose.

Accordingly, it has been considered desirable to develop a new and improved medical tubing for intravenous and intra-arterial applications for humans, or other animate creatures, which would overcome the foregoing difficulties and others while providing better and more advantageous overall results.

BRIEF SUMMARY OF THE INVENTION

In accordance with the invention, a tubing for intravenous and intra-arterial applications is provided.

More particularly in accordance with the invention, the tubing comprises a resilient conduit which is helically coiled along substantially its entire length. The conduit is pre-formed into a helical coil configuration so that when the conduit is in an unstressed condition, it assumes the helical coil configuration.

In accordance with another aspect of the invention, the conduit is self-storing.

In accordance with still another aspect of the invention, the conduit is made of a non-toxic plastic.

In accordance with yet another aspect of the invention, the conduit is made of a flexible plastic material.

According to another aspect of the invention, the conduit has a substantially circular cross-section. Preferrably, the conduit has a wall thickness of between approximately 0.001 inch and approximately 0.20 inches.

According to still another aspect of the invention, the conduit has a first end and a second end and further comprises a drip chamber provided on the conduit first end and a needle adaptor provided on the conduit second end. Preferably, a spike is provided on the free end of the drip chamber.

According to yet another aspect of the invention, the conduit includes a side-port to allow a second conduit to be placed into fluid communication with the conduit.

In accordance with yet still another aspect of the invention, the helical coil configuration of the conduit is such that each coil has approximately the same diameter as each other coil.

One advantage of the present invention is the provision of a new and improved tubing for human and other animate applications.

Another advantage of the present invention is the provision of an easily storable tubing for parenteral and peripheral intravenous administration systems as well as other intravenous and intra-arterial applications.

Still another advantage of the present invention is the provision of a tubing which is helically coiled along substantially its entire length. Accordingly, most of the tubing length would hang close to the fluid supply bag in its neutral position and would not become entangled in bedrails, sheets, pillowcases, naso-gastric tubes or other intravenous lines the way that conventional tubing presently does.

A further advantage of the present invention is that a much longer length of tubing can be conveniently incorporated in a helical coil configuration than in a straight piece of tubing. This will lengthen the range of movement of a patient to permit leaving a hospital bed to sit in a chair, go to the bathroom, etc.

Yet another advantage of the present invention is the provision of a coiled tubing for intravenous or intra-arterial applications which is useful in the operating room. In this environment, the coiled tubing lines would hang independently above the head of the anesthesiologist and would not collect on the floor, loop around the ether screen or become hopelessly ensnarled around other lines of tubing as present lines so often do.

Still other advantages and benefits of the present invention will become apparent to those skilled in the art upon a reading and understanding of the following detailed specification.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein:

FIG. 1 is a perspective exploded view of a tubing for intravenous applications according to the present invention; and, FIG. 2 is a perspective view of a parenteral administration system utilizing the tubing of FIG. 1.

DETAILED DESCRIPTION OF THE PREFERRED EMBODIMENT

Referring now to the drawings, wherein the showings are for purposes of illustrating a preferred embodiment of this invention only and not for purposes of limiting same, FIG. 1 shows the subject new tube A. Although the tube A is shown in the environment of an intravenous parenteral or peripheral line, it should be recognized that the invention has broader uses and can be used in other intravenous applications as well as in intra-arterial applications.

The tube A comprises a tube body 10 having therein a plurality of spaced coils 12, a first end 14 and a second end 16. Preferrably, the coils are so configured that each coil has approximately the same diameter as each other coil and the coils are equally spaced apart. It should, however, be recognized that other types of coil configurations, in which some coils are larger in diameter than others, or in which the coils are unevenly spaced apart, may be advantageous under some circumstances. Although fairly large coils 12 are illustrated in FIG. 1, it should be appreciated that smaller, more tightly wound coils, somewhat in the nature of a telephone cord (not illustrated), could also be provided according to the invention, if desired.

The tube body 10 is pre-formed into a helical coil configuration with the spaced coils 12 thereof assuming the coiled configuration whenever the tube is in an unstressed condition. In other words, the stretching of the tube body will not permanently distort the coiled shape. Rather, the tube body has an elastic memory which will return the body to essentially its original coiled shape when there is no stress on the body. However, the tube body 10 can be easily stretched, for example as the patient is moving without any risk of pulling a needle attached to the tubing out of the patient's arm. Also, the tube body can be stretched to allow the tube to be placed in a pump of the type now frequently used in the administration of intravenous solutions.

A drip chamber 18 is preferably provided on the first end 14 of the tube body 10. A spike 20 can extend from the free end of the drip chamber with a protector 22 enclosing the spike until it is put into use. If desired, a side port 24 can be provided at a selected point along the length of the tube body 10 so as to enable another tubing line to be placed in fluid communication with the tube. Of course, more than one side port can be provided on the tube body, if desired.

Adjacent to the second end of the tube body is a conventional roller clamp 30 and positioned on the second end 16 is a needle adaptor 32. A protector 36 encloses a free end of the needle adaptor until it is put into use. The coiled tubing A so far described is generally sterilized and housed in a sealed package so that it can be utilized in a sterile condition. The fluid path in the tube is advantageously sterile and nonpyrogenic.

The tubing A needs to be made from a non-toxic plastic material of the type which can be sterilized so that it can be used to transmit fluids and solutions into human beings or other animate creatures. Preferably, the conduit is made from a suitable conventional flexible plastic material. The conduit is shown as having a substantially circular cross-section, although it should be recognized that other types of cross-sections (e.g. oval or the like) can be useful and necessary in certain situations. The conduit can have a wall thickness of between approximately 0.001 inch and approximately 0.20 inches, as may be required for a particular use. The diameter of the conduit can vary as required for particular applications.

As mentioned, it should be noted that various types of tubing for animate applications could employ coiled tubing in accordance with the present invention. For example, Y-type blood sets (not illustrated) which employ a pair of tube lengths above a drip chamber and utilize three clamp-type flow regulators could be so constructed. In this instance, only the tubing below the drip chamber would be coiled in accordance with the present invention. Additionally, extension sets (not illustrated), which employ Luer adapters could be constructed from coiled tubing in accordance with the present invention.

Once the package is opened, the tubing A can then be applied in a parenteral administration system, such as is illustrated in FIG. 2. The protector 22 would be removed from the end of the spike 20 and the spike would be driven into a bag 50 containing a solution 52. The bag is generally hung on a hook 54 which is secured to a column 56 supported on a base 58. At some point during this procedure, the needle protector 36 would be removed and a needle 60 would be secured to the needle adaptor 32. Thereafter, the needle may be inserted into a vein of a patient (not illustrated). The solution 52 in the bag flows by gravity from the bag through the tubing A and the needle, into the patient's vein.

The roller clamp 30 can variably compress the tubing and thereby provide a variable rate of flow of the solution 52 through the tubing. However, it should be recognized that other means for controlling the flow of fluid through the tubing, such as the pump mentioned earlier, can also be provided.

There has been disclosed a new and improved tubing for intravenous and intra-arterial applications. The use of this tubing minimizes the risk of the tube becoming caught in bed sheets or the like or entangled in other lines or becoming hung up on protruding objects during movement of the patient. It also enables a patient to increase the range of his mobility without having to take the entire parenteral administration system with him. This tubing is also useful for anesthesiologists in minimizing clutter around an operating table by allowing coiled administration lines to hang independently at or above the head of the anesthesiologist instead of becoming entangled on the operating room floor.

The invention has been described with reference to a preferred embodiment. Obviously, alterations and modifications will occur to others upon a reading and understanding of this specification. It is intended to include all such modifications and alterations insofar as they come within the scope of the claims or the equivalents thereof.

What is claimed is:

1. A tube for intravenous and intra-arterial applications, comprising a resilient conduit made of a non-toxic plastic material which is helically coiled along substantially its entire length, wherein said conduit is pre-formed into a helical coil configuration so that when said conduit is in an unstressed condition, it assumes said helical coil configuration, said conduit including on a helical coil thereof a side port to allow a second conduit to be placed into fluid communication with said conduit.

2. The tube of claim 1 wherein said conduit is self-storing.

3. The tube of claim 1 wherein said conduit is made of a flexible plastic material.

4. The tube of claim 1 wherein said conduit has a substantially circular cross-section.

5. The tube of claim 1 wherein said conduit has a wall thickness of between approximately 0.001 inch and approximately 0.20 inches.

6. The tube of claim 1 wherein each coil of said helical coil configuration has approximately the same diameter as each other coil.

7. A parenteral administration system comprising:

a fluid supply container having an outlet;

a resilient helically coiled conduit having first and second ends wherein said conduit is helically coiled along substantially its entire length, said conduit first end being in fluid communication with said fluid supply container outlet, wherein said conduit is pre-formed into a helical coil configuration so that when said conduit is in an unstressed condition, it assumes a helical coil configuration, wherein said conduit including on a helical coil thereof a side port to allow a second conduit to be placed into fluid communication with said conduit, and wherein said conduit is made from a non-toxic plastic material; and, a needle having an inlet, said conduit second end being in fluid communication with said needle inlet.

8. The system of claim 7 further comprising a flow control means which is positioned on a portion of said conduit.

9. The system of claim 7 further comprising a drip chamber provided on said conduit first end.

* * * * *